United States Patent
Richardson et al.

(10) Patent No.: US 11,846,308 B2
(45) Date of Patent: Dec. 19, 2023

(54) QUICK RELEASE RESTRAINT RING

(71) Applicants: Jed C. Richardson, Batavia, IL (US); Abdullah Shahzad, Aurora, IL (US)

(72) Inventors: Jed C. Richardson, Batavia, IL (US); Abdullah Shahzad, Aurora, IL (US)

(73) Assignee: Norix Group, Inc., West Chicago, IL (US)

(*) Notice: Subject to any disclaimer, the term of this patent is extended or adjusted under 35 U.S.C. 154(b) by 124 days.

(21) Appl. No.: 17/195,622

(22) Filed: Mar. 8, 2021

(65) Prior Publication Data
US 2021/0186739 A1 Jun. 24, 2021

Related U.S. Application Data

(63) Continuation of application No. 15/871,057, filed on Jan. 14, 2018, now Pat. No. 10,980,660.

(51) Int. Cl.
| | | |
|---|---|---|
| *F16B 12/56* | (2006.01) | |
| *A61F 5/37* | (2006.01) | |
| *E05B 73/00* | (2006.01) | |
| *F16B 12/60* | (2006.01) | |

(52) U.S. Cl.
CPC ............ *F16B 12/56* (2013.01); *A61F 5/3769* (2013.01); *A61F 5/3792* (2013.01); *E05B 73/00* (2013.01); *F16B 12/60* (2013.01)

(58) Field of Classification Search
CPC ................. A61F 5/3769; A61F 5/3792; Y10T 403/1683; Y10T 403/592; F16B 12/56; F16B 12/60; F16B 21/165
See application file for complete search history.

(56) References Cited

U.S. PATENT DOCUMENTS

| | | | | |
|---|---|---|---|---|
| 410,130 | A * | 8/1889 | Whitus | F16B 12/60 5/298 |
| 1,392,581 | A * | 10/1921 | Leaf | F16B 12/56 5/287 |
| 1,922,388 | A * | 8/1933 | Norris | F16B 12/60 5/305 |
| 2,679,842 | A * | 6/1954 | Brill | A61F 5/3769 128/882 |
| 3,897,778 | A * | 8/1975 | Forbes-Robinson | A61F 5/3784 5/83.1 |
| 4,267,830 | A * | 5/1981 | Vick | A61F 5/3707 128/857 |
| 4,998,308 | A * | 3/1991 | Farago | A61F 5/3776 5/503.1 |

(Continued)

*Primary Examiner* — Matthew R McMahon
(74) *Attorney, Agent, or Firm* — James D Palmatier; Applied Patent Services

(57) ABSTRACT

The present invention comprises a kit of a restraint ring, a base and a quick release, tamper resistant fastener. The base is adapted to attach to a fixture. The fixture may be a bed, chair, floor or wall. The base may be attached to the bed, for example, by a connecting rod extending under the bed or pierced through the bed. The connecting rod may be adapted to receive a quick release fastener or threaded through fastener to secure the restraint ring to the connecting rod. The base may be seated in the sidewall if the rod is pierced through the bed or comprise a flange to bear on the bed. The base is adapted to releasably receive the quick release fastener thereby attaching the restraint ring to the base.

11 Claims, 12 Drawing Sheets

(56) References Cited

U.S. PATENT DOCUMENTS

| | | | | |
|---|---|---|---|---|
| 5,070,556 A | * | 12/1991 | Gloger | A47C 17/86 |
| | | | | 312/334.25 |
| 5,097,686 A | * | 3/1992 | Plumer | E05B 35/008 |
| | | | | 70/346 |
| 7,997,106 B2 | * | 8/2011 | Mahaffey | E05B 73/0005 |
| | | | | 70/49 |
| 8,007,059 B2 | * | 8/2011 | Karl | A47C 19/021 |
| | | | | 108/147.11 |
| 9,044,100 B1 | * | 6/2015 | Wang | A47C 19/20 |
| 9,661,933 B2 | * | 5/2017 | Karl | A47C 19/025 |
| 10,842,696 B1 | * | 11/2020 | Wolpe | A63B 21/0552 |
| 2019/0211860 A1 | * | 7/2019 | Yang | F16B 12/48 |

* cited by examiner

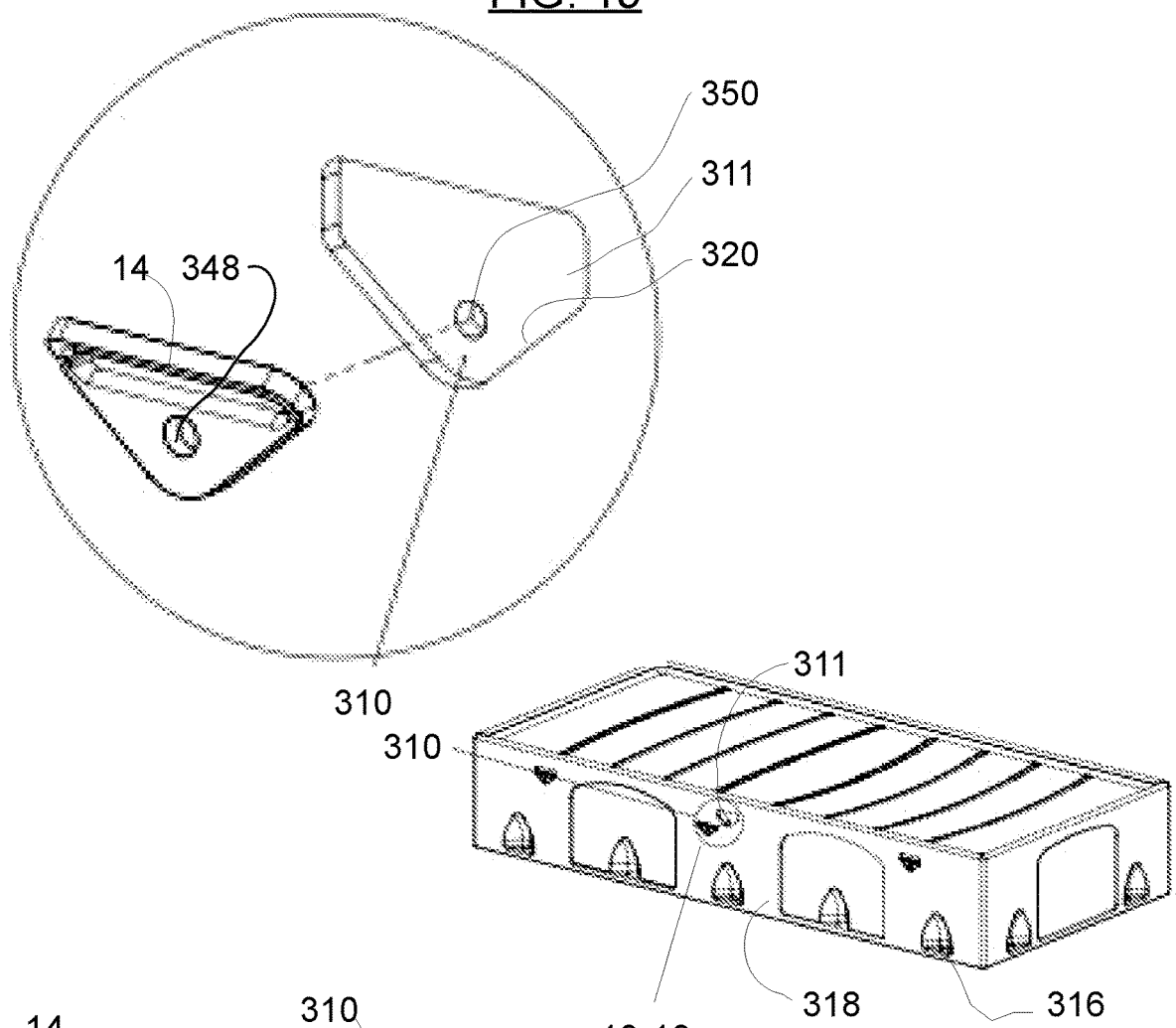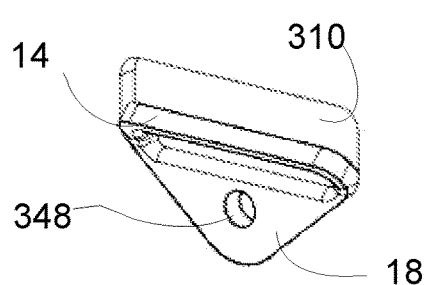

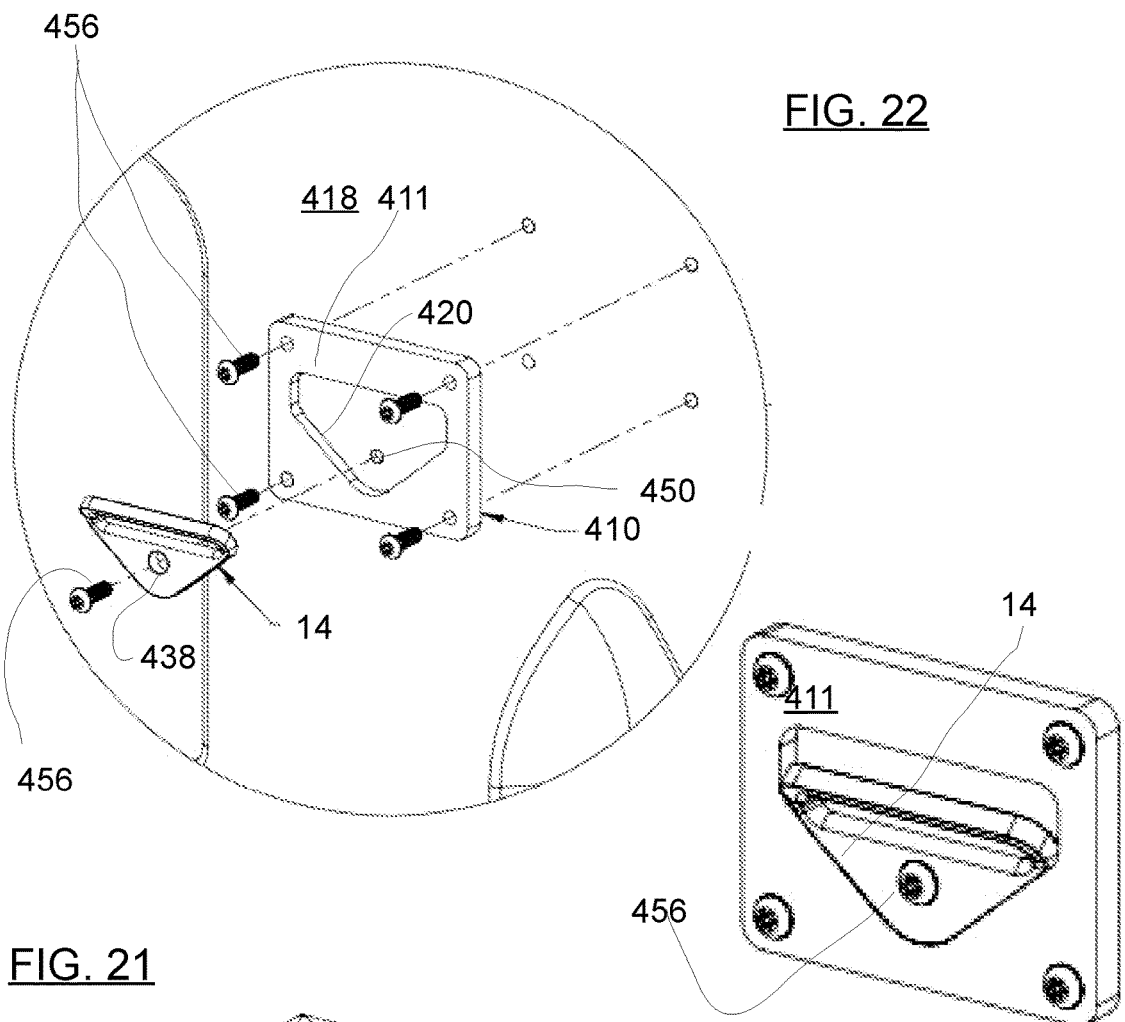
FIG. 22
FIG. 23
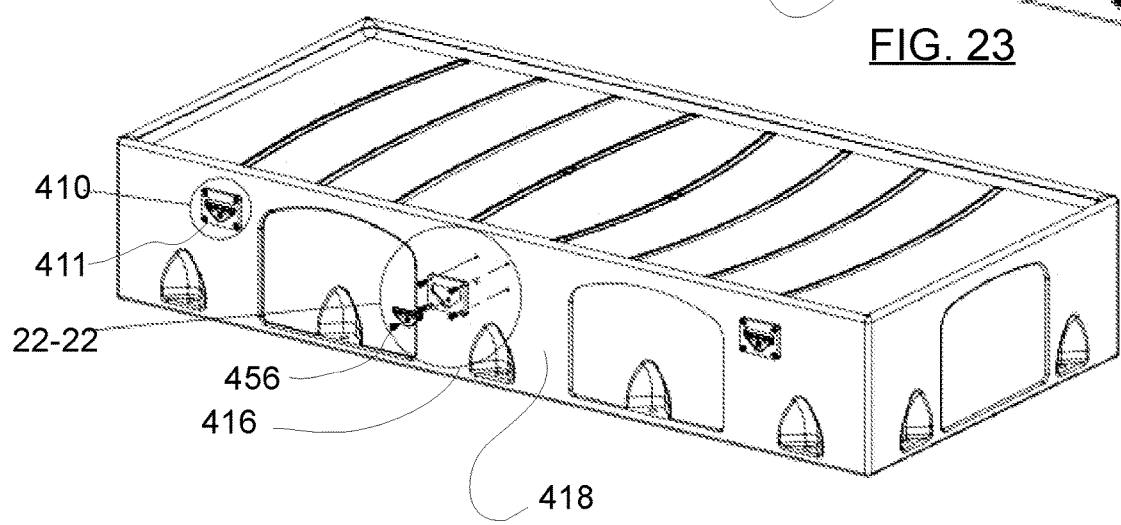
FIG. 21

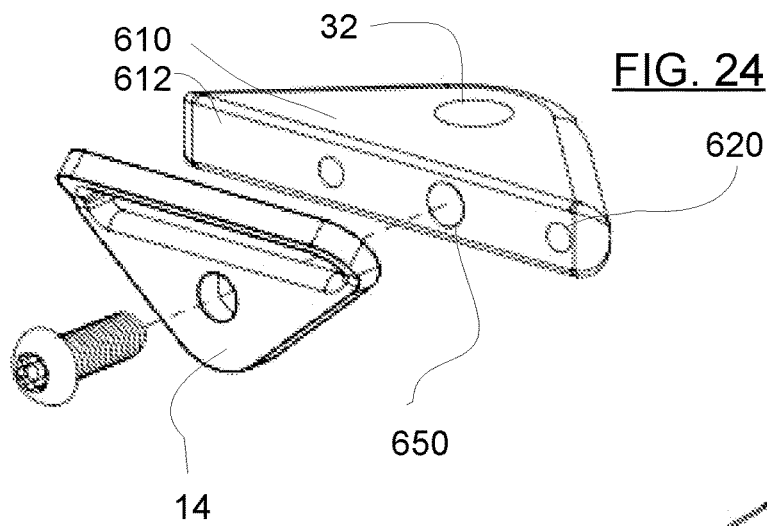
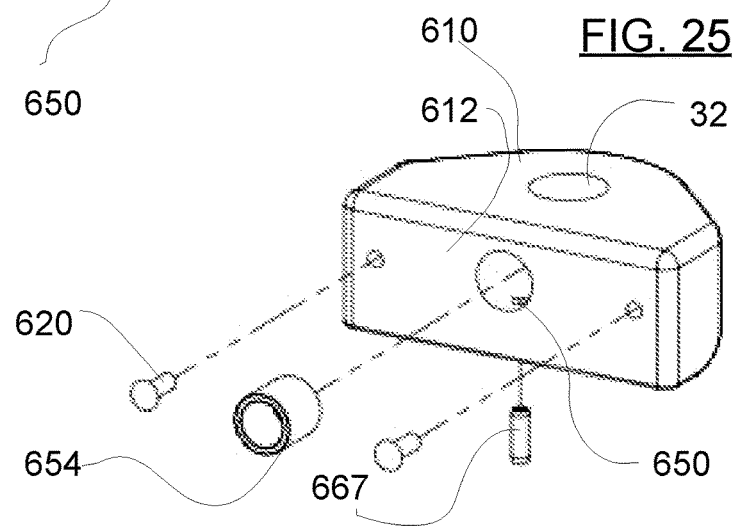
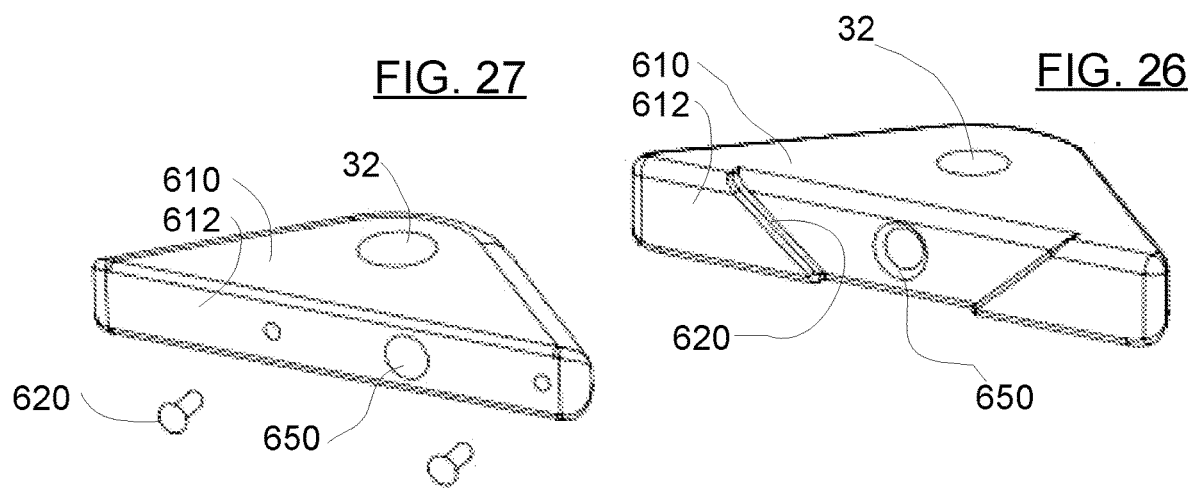

QUICK RELEASE RESTRAINT RING

RELATED APPLICATIONS

This application is a continuation of co-pending U.S. Non-provisional application Ser. No. 15/871,057, filed Jan. 14, 2018 entitled QUICK RELEASE RESTRAINT RING now U.S. Pat. No. 10,980,660.

FIELD OF THE INVENTION

The present invention relates generally to restraint rings used in facilities to attach individuals to an object to restrict their movement.

BACKGROUND OF THE INVENTION

Restraint rings have been used to restrain people for their own safety and for the safety of those around them. Restraint rings comprise a ring or fixture attached to a chair, bed or the floor. The ring is adapted to receive a strap, rope or chain that is looped through the ring and attaches to the subject to another ring to restrict movement. A restraint ring may be used with hand cuffs having one cuff on the subjects arm or leg and the other cuff attached to the restraint ring.

Restraint rings may also be used with straps to strap a subject to a bed or chair by connecting a first end of the strap to a first restraint ring, extending the strap over the subject having the subject between the strap and the bed and attaching a second end of the strap to a second restraint ring whereby the strap bears against the subject to restrain movement.

Restraint rings must be secured to be effective. The restraint ring should be anchored to a floor, wall or a piece of furniture that is anchored or ballasted to restrain movement. The restraint ring may be securely attached to a sturdy piece of furniture for restraining the subject to the furniture such as a bed or chair.

Restraint rings may be used in incarceration type situations such as jail or police holding areas as well as health care facilities to restrain patients. The sight of a restraint ring on a piece of furniture may be intimidating in a health care facility thus causing stress in the patient. Therefore, a quick release restraint ring is needed that can be easily and quickly attached and removed to a piece of furniture.

BRIEF SUMMARY OF THE PRESENT INVENTION

The present invention comprises a kit of a restraint ring, a base and a quick release, tamper resistant fastener. The base is adapted to attach to a fixture. The fixture may be a bed, chair, floor or wall. The base may be attached using tamper resistant fasteners. The base may be permanently attached or may be removably attached. The base is adapted to releasably receive the quick release fastener thereby attaching the restraint ring to the base. The base may be attached by a connector extending from a first side to a second side. The connector adapted to receive the quick release fastener thereby holding the restraint ring on the fixture. The restraint ring may be made of metal or plastic or a restraint material.

The quick release fastener engages the base and bears against the restraint ring to provide secure anchoring of the restraint ring. Actuating the quick release fastener disengages the base and allows the restraint ring to be removed.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE SEVERAL VIEWS OF THE DRAWING

FIG. 18 is a perspective view of the fourth embodiment of the present invention.

FIG. 19 is an exploded section view of the fourth embodiment of the present invention taken at approximately 19-19 of FIG. 18.

FIG. 20 is a section view of the fourth embodiment of the present invention taken at approximately 19-19 of FIG. 18.

FIG. 21 is a perspective view of a fifth embodiment of the present invention.

FIG. 22 is an exploded section view of the fifth embodiment of the present invention taken at approximately 22-22 of FIG. 21.

FIG. 23 is a section view of the fifth embodiment of the present invention taken at approximately 22-22 of FIG. 21.

FIG. 24 is a perspective exploded view of the first embodiment of the present invention.

FIG. 25 is a perspective exploded view of a sixth embodiment of the present invention.

FIG. 26 is a perspective exploded view of a seventh embodiment of the present invention.

FIG. 27 is a perspective exploded view of an eight embodiment of the present invention.

DETAILED DESCRIPTION OF THE INVENTION

Figure 1:
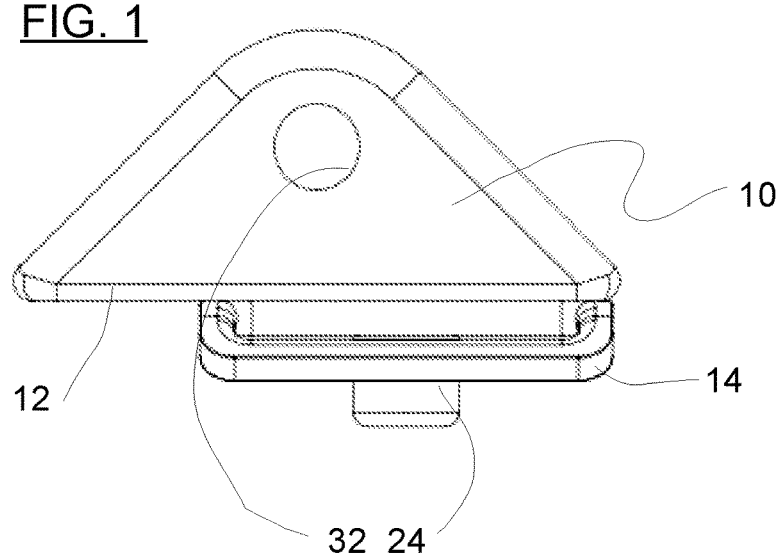
FIG. 1 is a top plan view of a first embodiment of the present invention.
Figure 2:
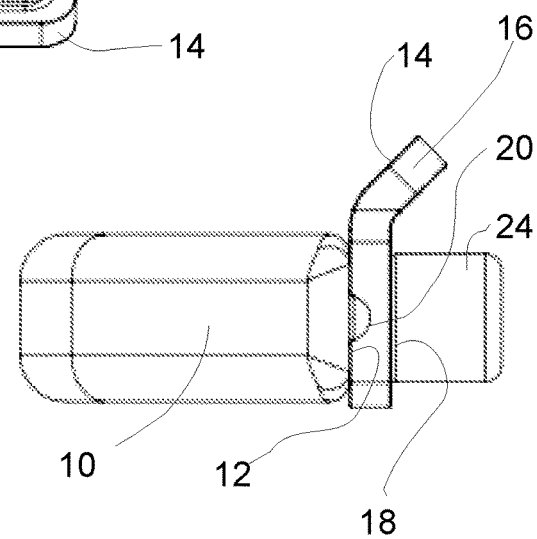
FIG. 2 is a right side elevation view of the first embodiment of the present invention of FIG. 1
Figure 3:
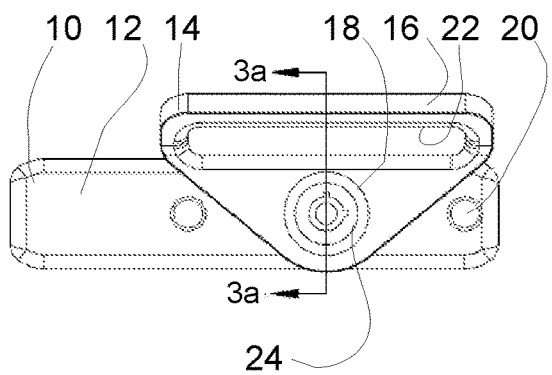
FIG. 3 is a front elevation view of the first embodiment of the present invention of FIG. 1.
Figure 3A:
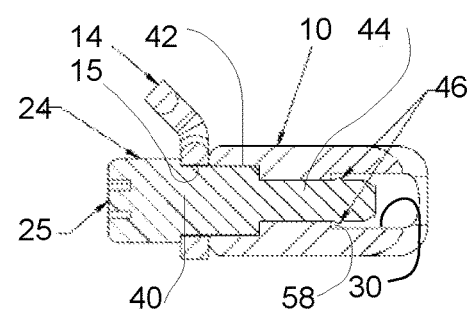
FIG. 3a is a section view of the first embodiment taken at approximately 3a-3a of FIG. 3.
Figure 4:
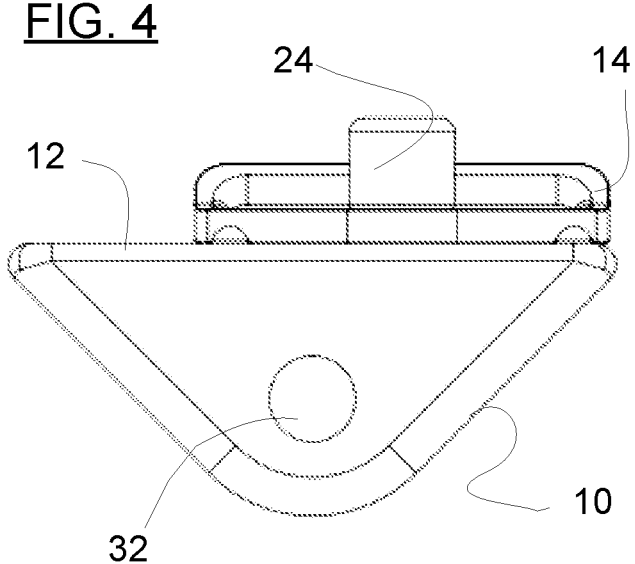
FIG. 4 is a bottom plan view of the first embodiment of the present invention of FIG. 1.
Figure 5:
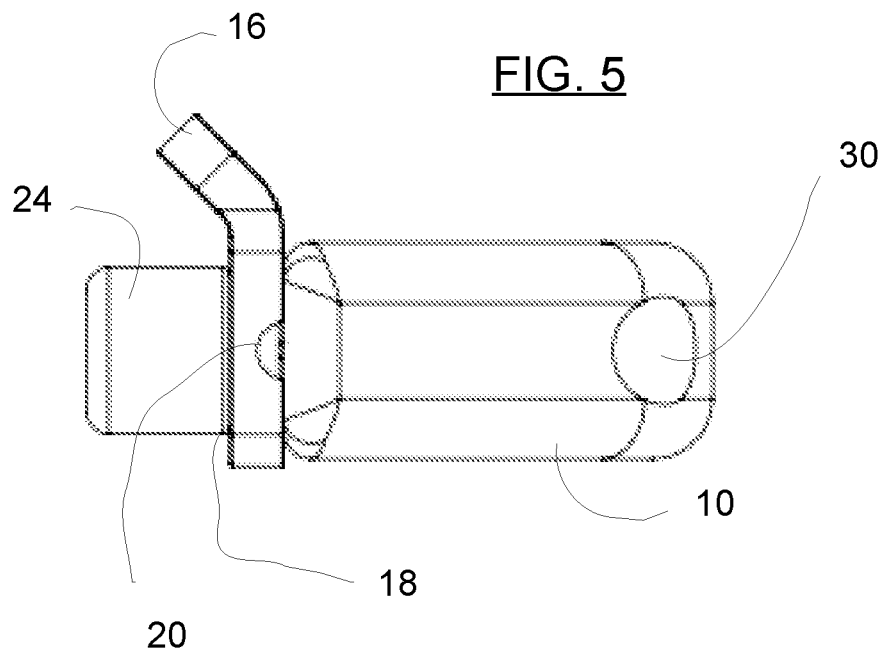
FIG. 5 is a left plan view of the first embodiment of the present invention of FIG. 1.
Figure 6:
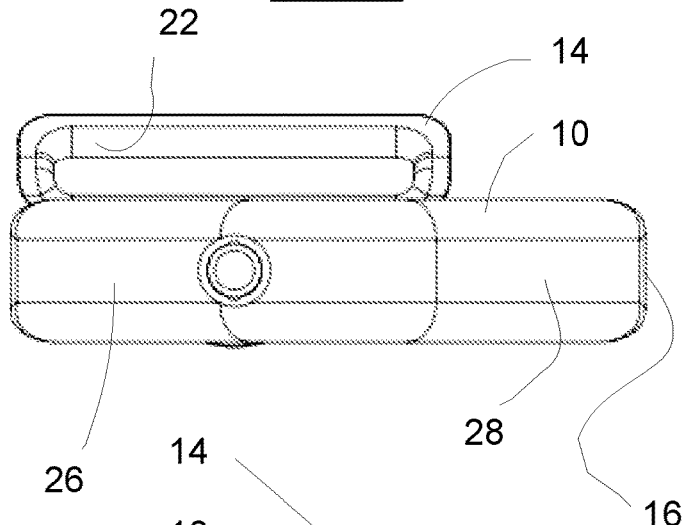
FIG. 6 is a back elevation view of the first embodiment of the present invention of FIG. 1.
Figure 7:
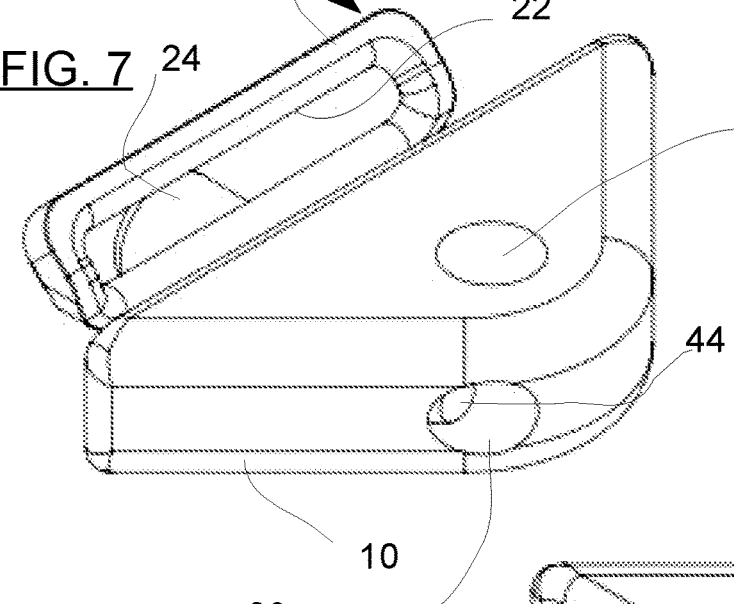
FIG. 7 is a top back perspective view of the first embodiment of the present invention of FIG. 1
Figure 8:
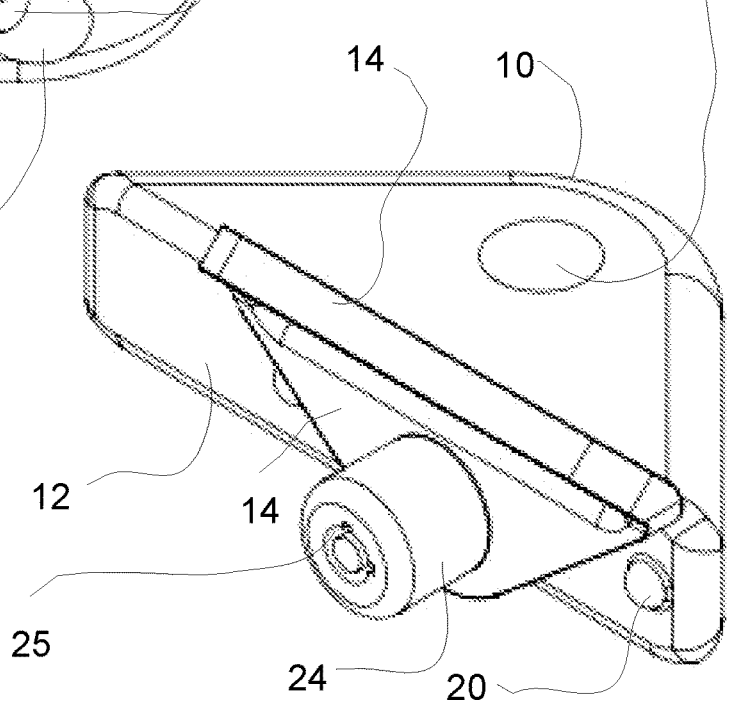
FIG. 8. is a top front perspective view of the first embodiment of the present invention of FIG. 1.
Figure 9:
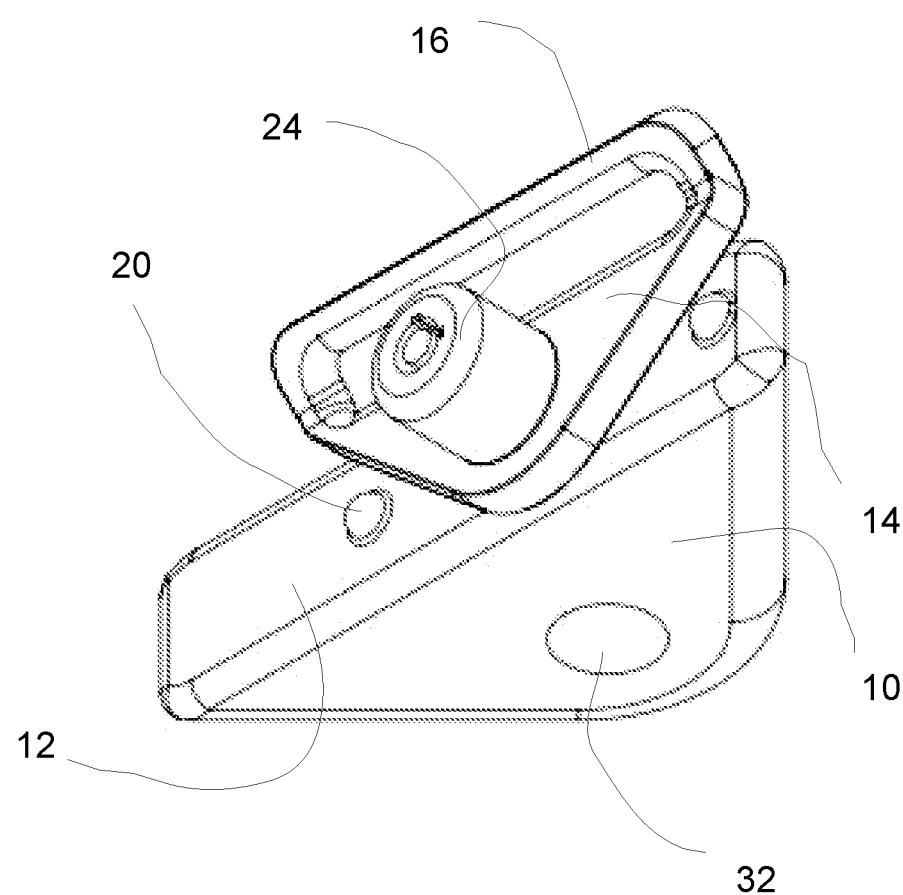
FIG. 9 is a bottom front perspective view of the first embodiment of the present invention of FIG. 1.
Figure 10:
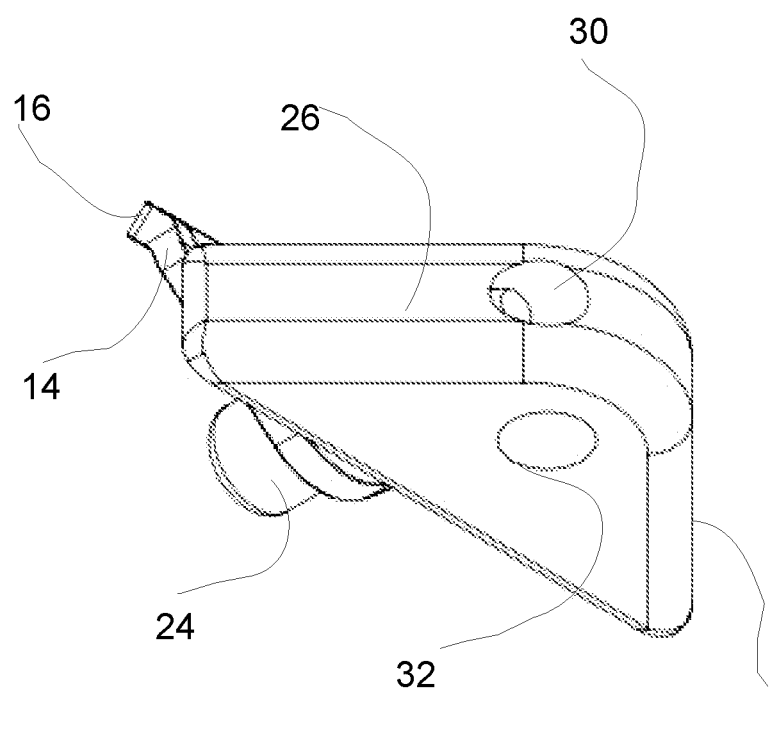
FIG. 10 is a bottom front perspective view of the first embodiment of the present invention of FIG. 1.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention. It is to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting. It should be appreciated that the invention can be used for any suitable.

Referring to FIGS. 1-5 the invention comprises a base 10 having a mounting surface 12 and a restraint ring 14 attached to the mounting surface 12. The restraint ring 14 has an open loop portion 16 and a ring base 18. Mounting hole 15 extends through base 10. Quick release fastener 24 extends through ring base 18 into quick release hole 30. Quick release fastener 24 engages base 10 to secure restraint ring 14 to base 10. Stabilizers 20 on mounting surface 12 to urge restraint ring 14 to maintain a predetermined orientation with respect to base 10. It is preferable that open loop portion 16 is spaced from base 10. Quick release fastener 24 comprises head 40 bearing against restraint ring 14 to attach restraint ring 14 to base 10 having ring shaft extending through ring 14 and into base 10 with quick release shaft extending on quick release hole 30 to dispose locking mechanism 46 in position to bear against locking shoulder 58.

Referring to FIGS. 6-10, base 10 has a first side 26 and second side 28. Quick release hole 30 opens to first side 26 having quick release shaft 44 removably attached therein. Restraint ring 14 comprises strap opening 22 on open loop portion 16. Secure hole 32 extends through base 10 generally perpendicular to quick release hole 30. Quick release fastener 24 may have a release mechanism 25 adapted to securely release and prevent unauthorized removal of restraint ring 14.

Figure 11:
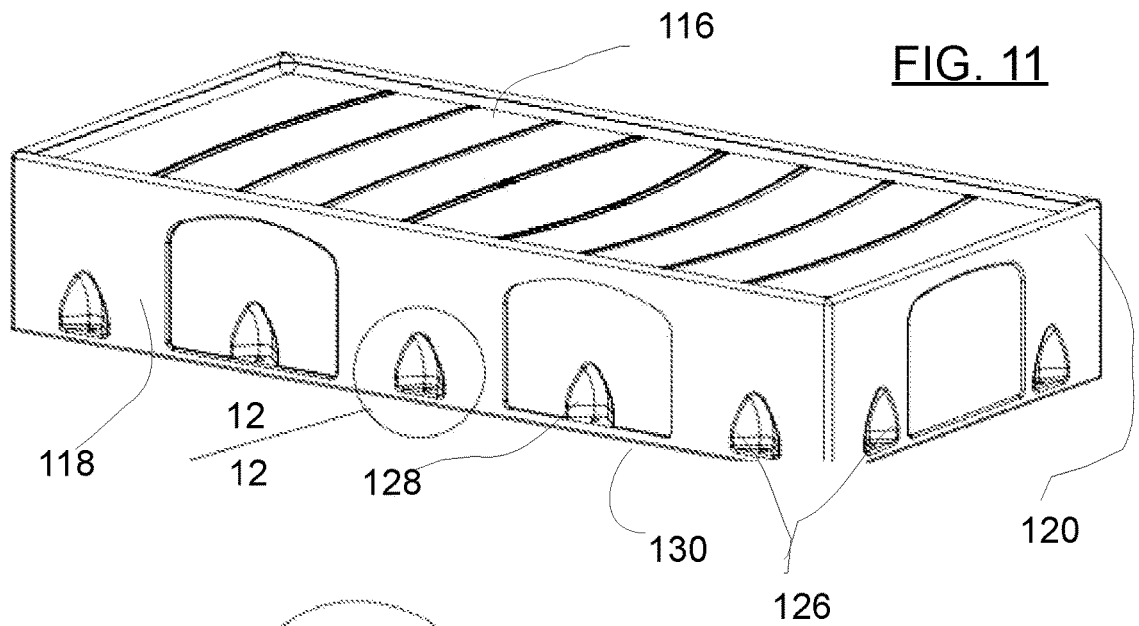
FIG. 11 is a perspective view of a bed adapted to attach to the first embodiment of the present invention of FIG. 1.
Figure 12:
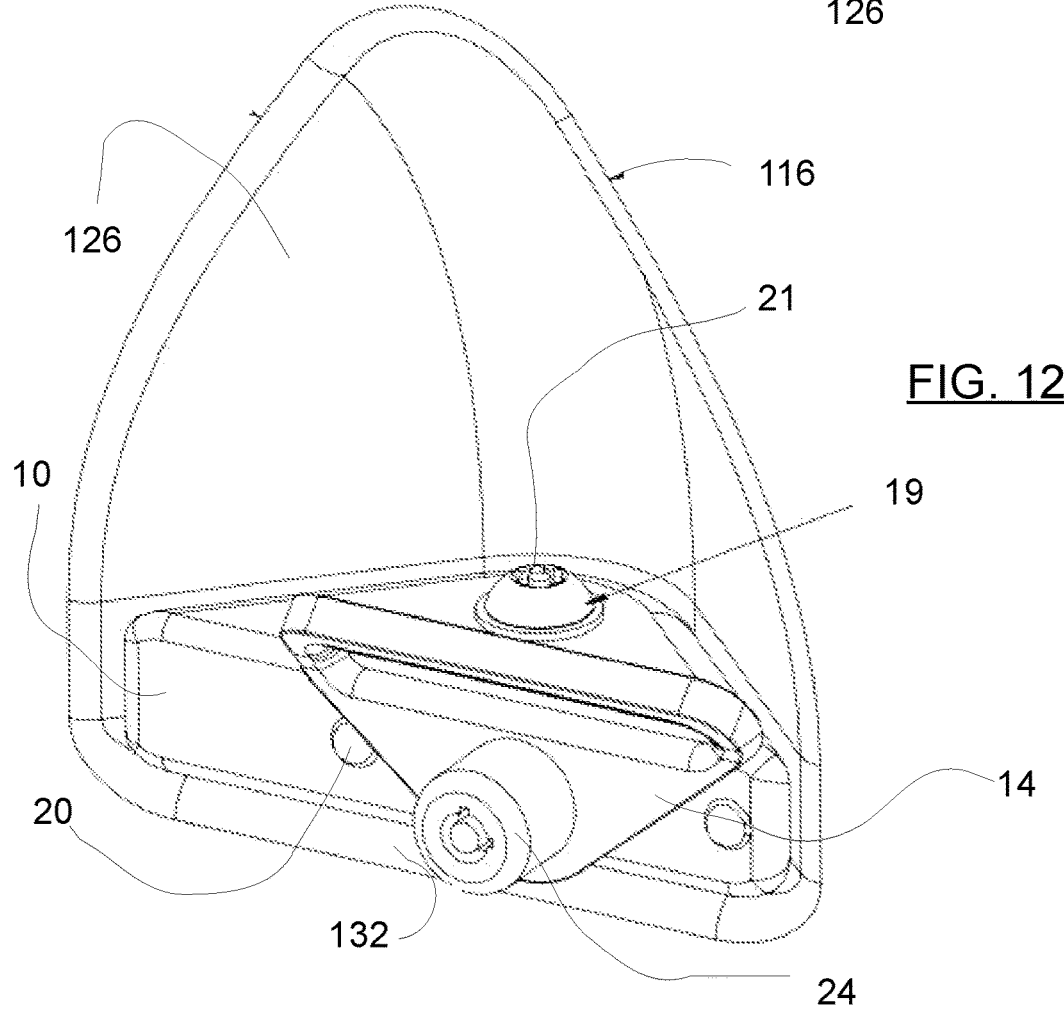
FIG. 12 is a section view of the first embodiment of the present invention of FIG. 1 attached to the bed of FIG. 11 taken at approximately 12-12 of FIG. 11.

Referring to FIG. 11-12, bed 116 may have a side wall 118 having fastener coves 128 molded therein adjacent the bed bottom 130. Cove 128 comprises a side wall 126 and bottom wall 132. Anchor fastener 19 extends through base 10 to engage bottom wall 132 to removably attach base 10 to bed 116. Anchor fastener 19 may be a threaded fastener having a tamper resistant head 21. Anchor fastener may alternatively attach base 10 to floor or wall.

Figure 13:
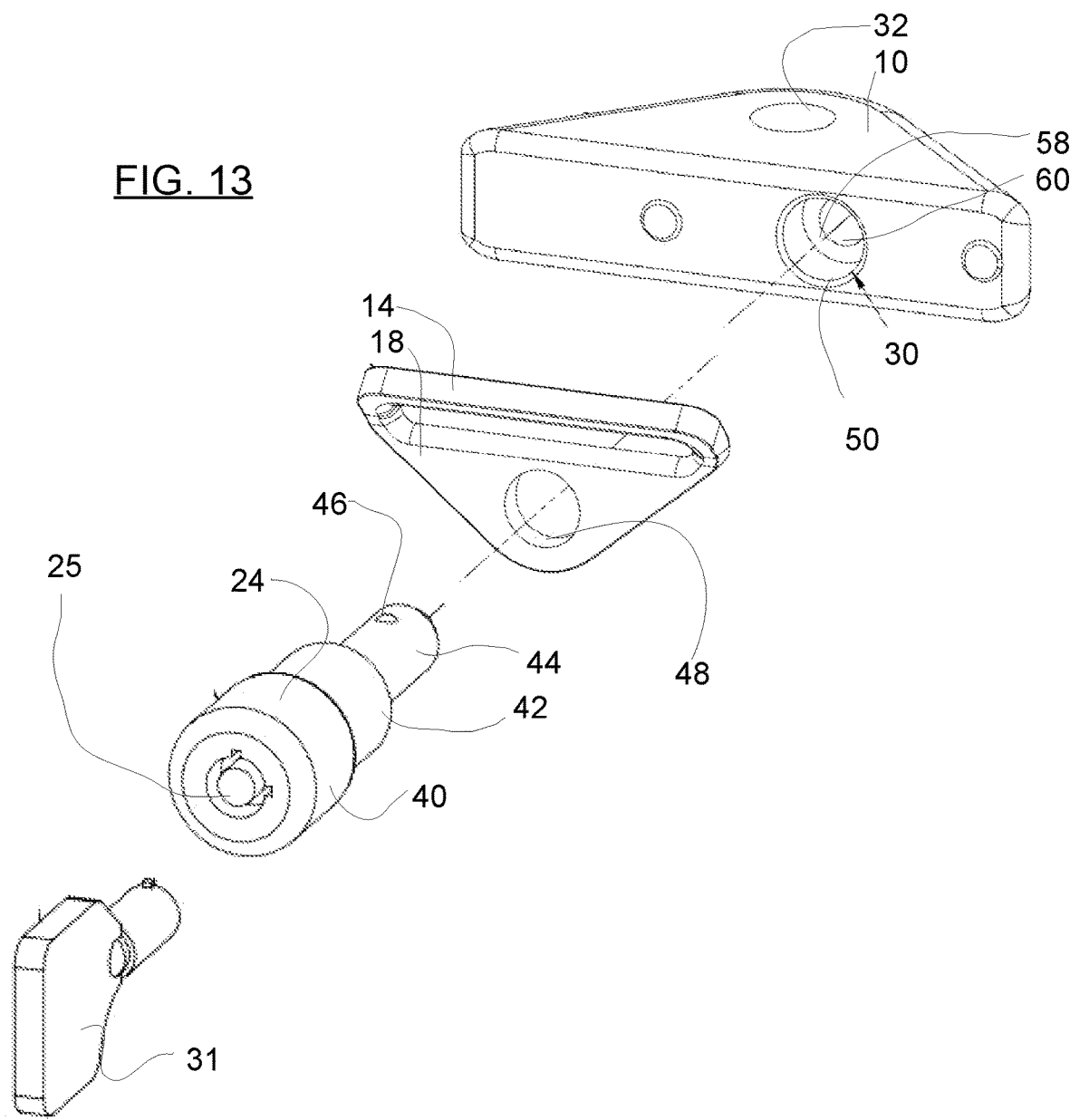
FIG. 13 is an exploded view of the first embodiment of the present invention.

Referring to FIG. 13. Quick release fastener 24, may have locking head 40 with release mechanism 25. Release mechanism 25 may be operated by actuator 31 adapted to release quick release fastener 24 from base 10. Release mechanism 25 may be a key, a magnetic actuator, a bio-metric scanner, a remote control release, a combination lock or other actuator device. Quick release fastener 24 may comprise a head 40 having a ring shaft 42 extending therefrom. A base shaft 44 may extend from ring shaft 42. Base shaft 44 may have locking mechanism 46 contained therein. Locking mechanism 46 may have retractable fixtures extending perpendicular to base shaft 44. Locking mechanism 46 may be actuated by release mechanism 25.

Continuing to refer to FIG. 13, quick release hole 30 may comprise ring opening 50 and locking shoulder 58 and shaft portion 60. Restraint ring 14 may have a restraint hole 48 extending there-through. When assembled, ring shaft 42 is adapted to extend into shaft portion. Locking mechanism 46 releasably engages locking shoulder 58. ring shaft extends through restraint hole 48 and into ring opening 50. Release mechanism 25 actuates the locking mechanism 46 into a non-locking configuration whereby quick release fastener is extended through restraint hole 48 and into base 10 at quick release hole 30. Base shaft 44 in shaft portion 60 is adapted to hold locking mechanism adjacent locking shoulder 58. Release mechanism 25 may be disengaged to extend locking mechanism 46 adapted to bear against locking shoulder 58. Head 40 bears against ring base 18 thereby removably securing restraint ring 14 to base 10.

Figure 14:
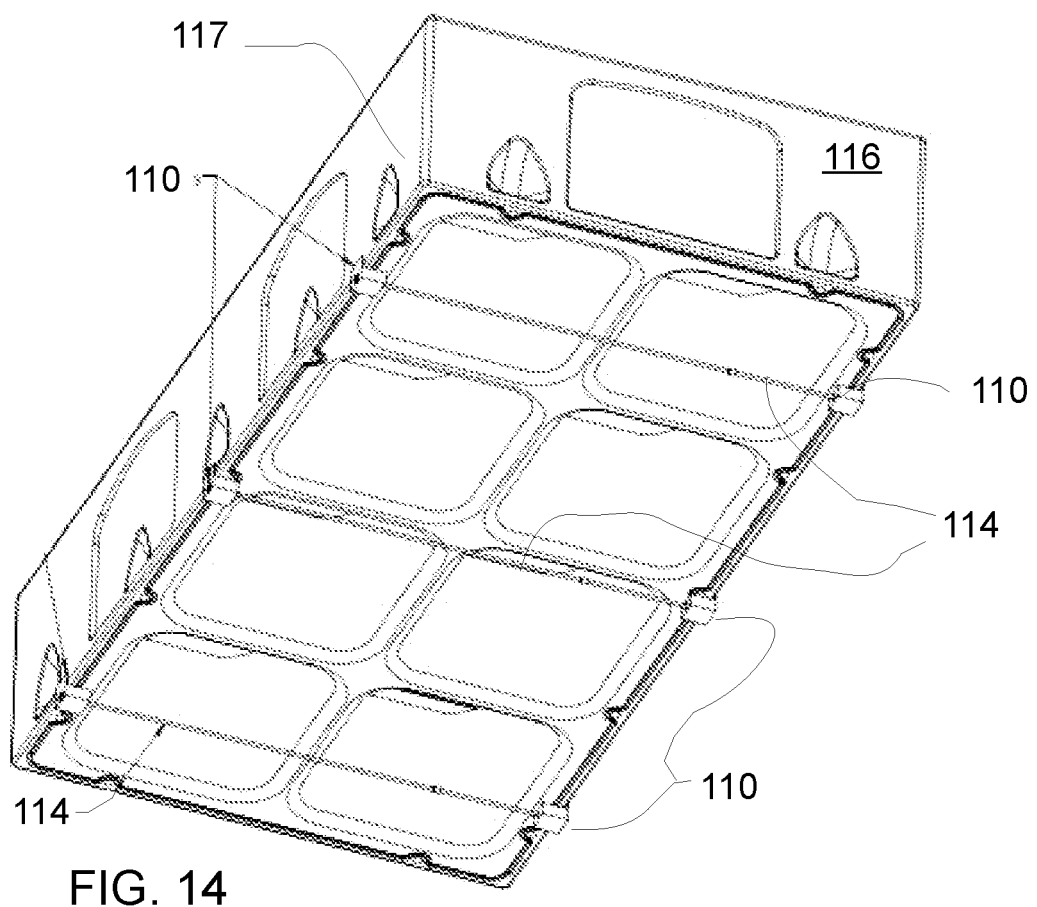
FIG. 14 is a bottom perspective view of a second embodiment of the present invention attached to a bed.
Figure 15:
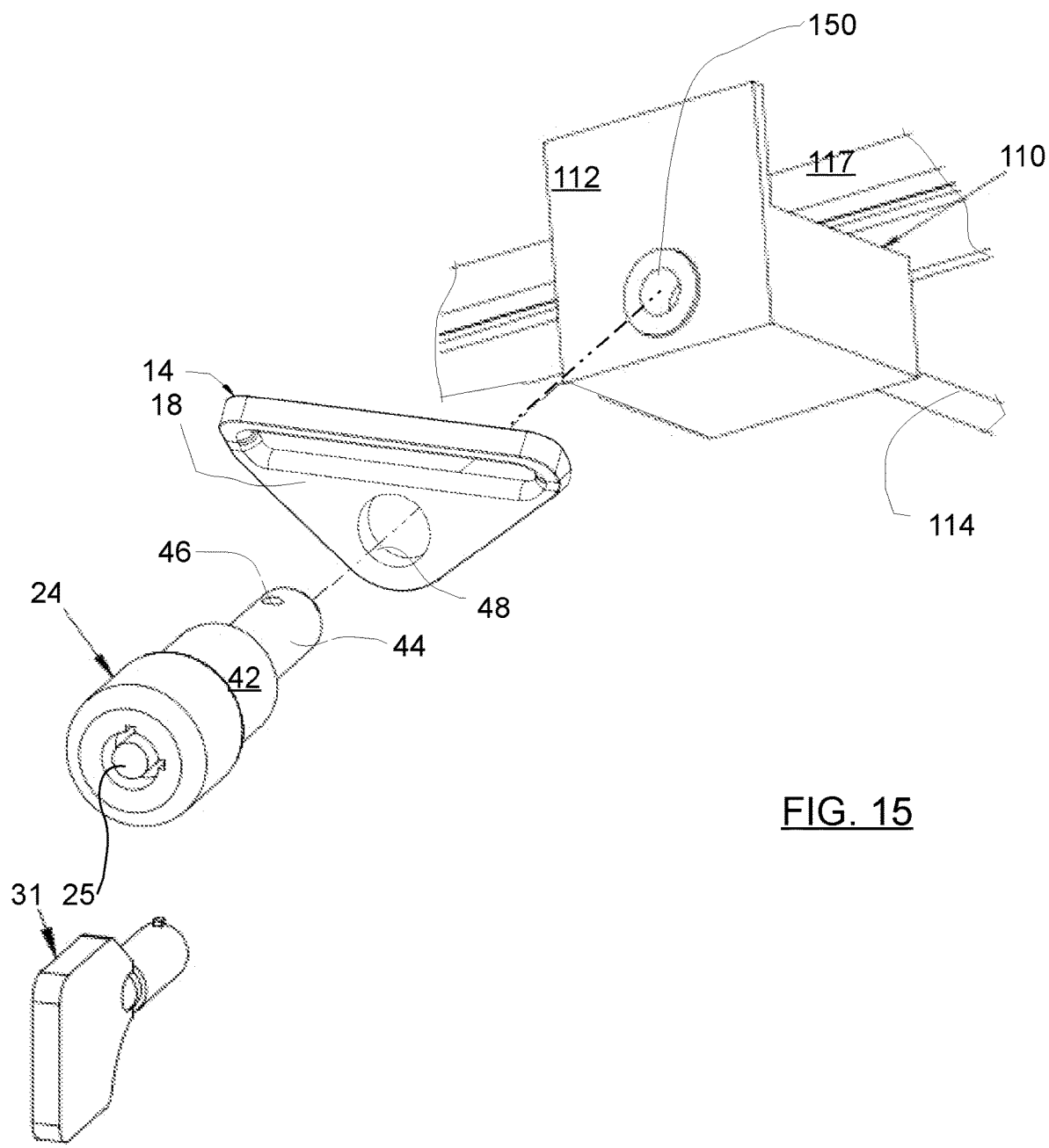
FIG. 15 is a perspective view of the second embodiment of the present invention.

Referring to FIGS. 14 and 15, base 110 may be attached to bed 116 comprising two opposing sidewalls 117 by connector rod 114 extended under bed 116. Connector rod 114 may be attached to first and second base 110. First and second base 110 bear against opposing respective sidewalls 117 to dispose ring opening 150 adjacent to the respective sidewalls 117, the ring opening 150 adapted to receive quick release fastener 24. Base 110 may have flange 112 bearing against bed 116.

Figure 16:
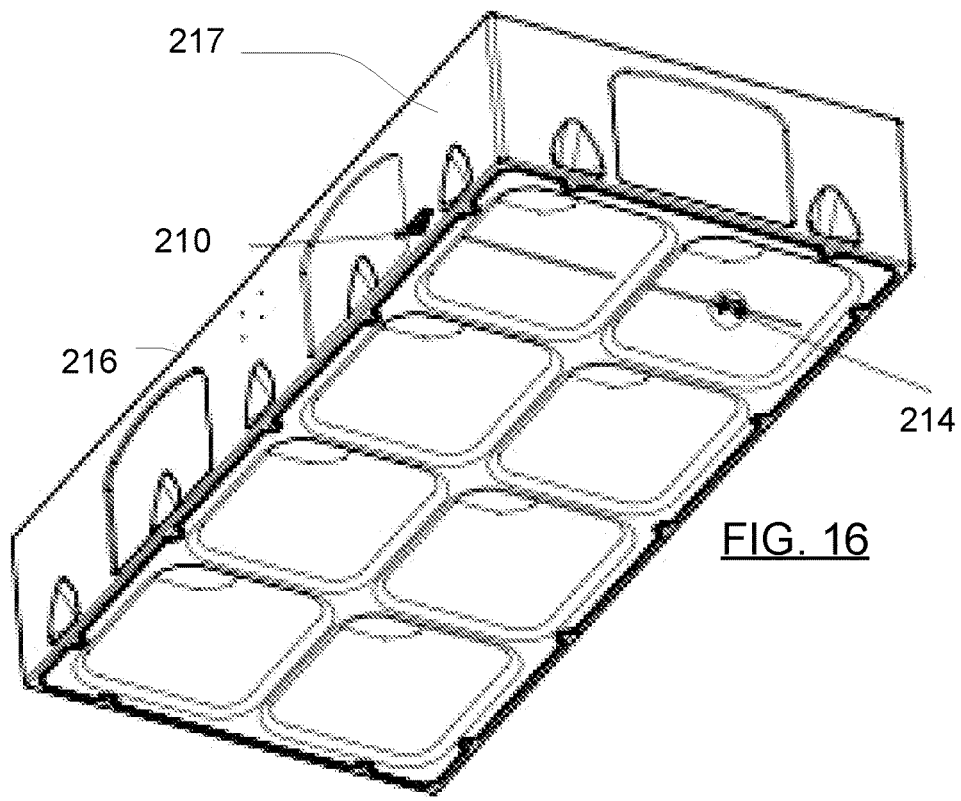
FIG. 16 is a perspective view of a third embodiment of the present invention.
Figure 17:
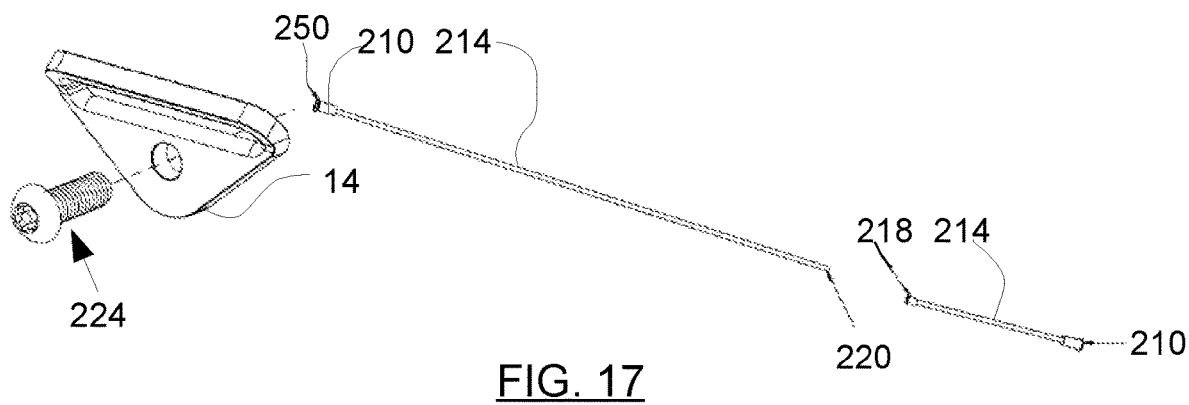
FIG. 17 is an exploded view of the third embodiment of the present invention.

Referring to FIGS. 16 and 17, base 210 may comprise ring opening 250 on the end of shaft 214. Shaft 214 may be pierced through bed 216. Ring opening 250 may be adapted to removably receive quick release fastener 224. Quick release fastener 224 may releasably connect restraint ring 14 to bed 216. Threaded coupling 218, 220 may be used to adapt shaft 214 to dispose base 210 on outside wall 217 of bed 216.

Referring to FIGS. 18-20, base 310 may comprise a pocket 311 formed on a molded bed 316. Pocket 311 may further comprise ring opening 350 and stabilizer edge 320 adapted to engage restraint ring 14 to hold restraint ring 314 in a predetermined orientation. Restraint hole 348 is disposed to align with ring opening 350.

Referring to FIGS. 21-23, base 410 may comprise bolt on pocket 411 attached to bed wall 418. Bolt on pocket 411 may comprise a restraint plate 416 comprising a ring opening 450 and stabilizer edge 420. Restraint ring 14 may fit in pocket 411 having ring opening 450 aligned with restraint hole 438. Tamper resistant quick turn fastener 456 may be adapted to removably attach restraint ring 14 to bolt on pocket 411.

Referring to FIGS. 24-27, base 610 may have different dimensions or have stabilizer 620 formed in front surface 612. Ring opening 650 may have insert 654 attached by pin 667. Ring opening 650 may be centered on front 612.

In summary base 10 may be attached to bed 16. Base 10 is adapted to releasably connect to restraint ring 14. Quick release fastener 24 extends through restraint ring 14 to releasably attach to base 10. Quick release fastener 24 may be tamper resistant having mechanical, electrical or other quick release lock.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given. Further, the present invention has been shown and described with reference to the foregoing exemplary embodiments. It is to be understood, however, that other forms, details, and embodiments may be made without departing from the spirit and scope of the invention which is defined in the following claims.

We claim:

1. A quick release restraint for releasably attaching to a bed having two opposing sidewalls, the quick release restraint comprising:
    a restraint ring having a ring base and an open loop portion, the ring base having a quick release hole therein;
    a connector rod, a first base and a second base, the connector rod on the bed, the first base comprising a ring opening and a flange, the flange on one of the opposing sidewalls, the second base comprising a second ring opening and a second flange, the second flange on the other of the two opposing sidewalls, the connector rod on the first base, the second base on the connector rod whereby the connector rod extends from the first base to the second base, the first base ring opening spaced from the connector rod, the second base ring opening spaced from the connector rod, the restraint ring base on the first base wherein the first base ring opening is concentric to the quick release hole, the open loop portion spaced from the first base and the first base is between the ring base and the connector rod; and
    a quick release fastener, the quick release fastener comprising a base shaft and a head, the base shaft on the head, the base shaft in the quick release hole and the first base connector opening whereby the ring base is between the head and the first base.

2. The quick release restraint of claim 1, further comprising a flange on the first base, the flange disposed on one of the two opposing sidewalls.

3. The quick release restraint of claim 2 wherein the connector rod extends under the bed.

4. The quick release restraint of claim 1, wherein the connector rod extends through the bed.

5. The quick release restraint of claim 4, further comprising a threaded coupling on the connector rod.

6. The quick release restraint of claim 5, wherein the connector rod is adapted to adjustably space the first base from the second base by the threaded coupling.

7. The quick release restraint of claim 1, further comprising a threaded connection between the quick release fastener and the first base.

8. A quick release restraint for releasably attaching a restraint ring to a bed, the bed comprising two opposing side walls, the quick release restraint comprising:
    a restraint ring, the restraint ring comprising a ring base and an open loop portion, the ring base comprising a restraint hole;
    a connector rod, the connector rod further comprising a first base and a second base, the connector rod extending through the bed and extending from each of the opposing sidewalls, the first base on one of the two opposing side walls, the second base on the other of the two opposing side walls, the connector rod on the first base, the connector rod on the second base whereby the first base is connected to the second base, each of the first base and second-base comprising a ring opening; and
    a fastener, the fastener comprising a head and a base shaft, the base shaft on the head, the base shaft disposed in the first base ring opening, the base shaft in the restraint hole, the base shaft is attached to the first base, the restraint hole between the head and the first base, and the first base between the restraint ring and the one of the two opposing sidewalls, whereby the open loop portion is spaced from the first base, the head on the ring base, whereby the restraint ring is attached to the bed.

9. The quick release restraint of claim 8, further comprising a coupling on the connector rod, the coupling adapted to adjustably space the first base from the second base.

10. The quick release restraint of claim 9, wherein the fastener is actuated by a key.

11. The quick release restraint of claim 9, wherein the fastener is threadably engaged to the base.

* * * * *